US009241947B2

(12) United States Patent
Reddy et al.

(10) Patent No.: US 9,241,947 B2
(45) Date of Patent: *Jan. 26, 2016

(54) BORONIC ACID DERIVATIVES AND THERAPEUTIC USES THEREOF

(71) Applicant: Rempex Pharmaceuticals, Inc., San Diego, CA (US)

(72) Inventors: Raja Reddy, San Diego, CA (US); Tomasz Glinka, Cupertino, CA (US); Maxim Totrov, San Diego, CA (US); Scott Hecker, Del Mar, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/829,062

(22) Filed: Mar. 14, 2013

(65) Prior Publication Data

US 2014/0194381 A1 Jul. 10, 2014

Related U.S. Application Data

(60) Provisional application No. 61/749,204, filed on Jan. 4, 2013.

(51) Int. Cl.
| | | |
|---|---|---|
| *A61K 31/69* | (2006.01) | |
| *A61K 45/06* | (2006.01) | |
| *A61K 31/407* | (2006.01) | |
| *A61K 31/4196* | (2006.01) | |
| *A61K 31/427* | (2006.01) | |
| *A61K 31/546* | (2006.01) | |
| *C07F 5/02* | (2006.01) | |

(52) U.S. Cl.
CPC .............. *A61K 31/69* (2013.01); *A61K 31/407* (2013.01); *A61K 31/4196* (2013.01); *A61K 31/427* (2013.01); *A61K 31/546* (2013.01); *A61K 45/06* (2013.01); *C07F 5/025* (2013.01)

(58) Field of Classification Search
CPC ........ C07F 5/025; A61K 31/69; A61K 38/00; A01N 55/08; C07K 5/06191
See application file for complete search history.

(56) References Cited

U.S. PATENT DOCUMENTS

| | | |
|---|---|---|
| 4,194,047 A | 3/1980 | Christensen et al. |
| 4,260,543 A | 4/1981 | Miller |
| 4,409,214 A | 10/1983 | Takaya et al. |
| 4,822,786 A | 4/1989 | Zama et al. |
| 5,442,100 A | 8/1995 | Bjorkquiest et al. |
| 5,888,998 A | 3/1999 | Maiti et al. |
| 6,184,363 B1 | 2/2001 | Shoichet et al. |
| 6,586,615 B1 | 7/2003 | Kettner et al. |
| 7,271,186 B1 | 9/2007 | Shoichet et al. |
| 7,439,253 B2 | 10/2008 | Lampilas et al. |
| 7,582,621 B2 | 9/2009 | Baker et al. |
| 7,612,087 B2 | 11/2009 | Aszodi et al. |
| 8,680,136 B2 | 3/2014 | Hirst et al. |
| 2004/0019203 A1 | 1/2004 | Micetich et al. |
| 2004/0157826 A1 | 8/2004 | Lampilas et al. |
| 2005/0020572 A1 | 1/2005 | Aszodi et al. |
| 2006/0019116 A1 | 1/2006 | Conley et al. |
| 2006/0178357 A1 | 8/2006 | Buynak et al. |
| 2006/0210883 A1 | 9/2006 | Chen et al. |
| 2010/0056478 A1 | 3/2010 | Desarbre et al. |
| 2010/0120715 A1 | 5/2010 | Burns et al. |
| 2010/0256092 A1 | 10/2010 | Xia et al. |
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194284 A1 | 7/2014 | Majmudar et al. |
| 2014/0194382 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |

FOREIGN PATENT DOCUMENTS

| | | |
|---|---|---|
| EP | 1550657 A1 | 7/2005 |
| FR | 2574070 A1 | 11/1984 |
| JP | 2003-229277 | 8/2003 |
| JP | 2004-291253 | 10/2004 |
| WO | WO 87/05297 | 9/1987 |
| WO | WO 89/10961 | 11/1989 |
| WO | WO 98/56392 A1 | 12/1998 |
| WO | WO 00/35904 A1 | 6/2000 |
| WO | WO 00/35905 A1 | 6/2000 |
| WO | WO 01/23374 A1 | 4/2001 |
| WO | WO 01/30149 | 5/2001 |

(Continued)

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.
Adediran et al., "A 'cephalosporin-like' cyclic depsipeptide: Synthesis and reaction with beta-lactam-recognizing enzymes", Bioorg Med Chem Lett. (1999) 9(3):341-346.
Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

(Continued)

*Primary Examiner* — San-Ming Hui
*Assistant Examiner* — Andrew Lee
(74) *Attorney, Agent, or Firm* — Knobbe Martens Olson & Bear LLP

(57) ABSTRACT

Disclosed herein are antimicrobial compounds compositions, pharmaceutical compositions, the use and preparation thereof. Some embodiments relate to boronic acid derivatives and their use as therapeutic agents.

37 Claims, No Drawings

(56) References Cited

FOREIGN PATENT DOCUMENTS

| WO | WO 02/22137 A1 | 3/2002 |
|---|---|---|
| WO | WO 02/083884 | 10/2002 |
| WO | WO 03/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2012/021455 A1 | 2/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/122888 A2 | 8/2013 |
| WO | WO 2014/089365 A1 | 6/2014 |
| WO | WO 2014/151958 A1 | 9/2014 |

OTHER PUBLICATIONS

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

Allen et al., "Ansel's Pharmaceutical Dosage Forms and Drug Delivery Systems", 8th Edition (2004) TOC only.

Arya et al., "Advances in asymmetric enolate methodology", Tetrahedron (2000) 56:917-947.

Babic et al., "What's new in antibiotic resistance? Focus on beta-lactamases", Drug Res Updates (2006) 9:142-156.

Bassetti et al., "New antibiotics for bad bugs: where are we?", Ann Clin Microbiol Antimicrob. (2013) 12:22-36.

Becker, Daniel E., "Antimicrobial Drugs", Anesth Prog (2013) 60:111-123.

Beenen et al., "Asymmetric copper-catalyzed synthesis of alpha-amino boronate esters from N-tert-butanesulfinyl aldimines", J Am Chem Soc. (2008) 130(22):6910-6911.

Biedrzycki et al., "Derivatives of tetrahedral boronic acids", J. Organomet. Chem. (1992) 431:255-270.

Bou et al., "Cloning, nucleotide sequencing, and analysis of the gene encoding an AmpC beta-lactamase in Acinetobacter baumannii", Antimicrob Agents Chemother (2000) 44(2):428-432.

Bou et al., "OXA-24, a novel class D beta-lactamase with carbapenemase activity in an Acinetobacter baumannii clinical strain", Antimicrob Agents Chemother (2000) 44(6):1556-1561 and Erratum Antimicrob Agents Chemother (2006) 50(6) 2280.

Brabez et al., "Design,synthesis, and biological studies of efficient multivalent melanotropin ligands: tools toward melanoma diagnosis and treament", J Med Chem. (2011) 54(20):7375-7384.

Brosz et al., "Resolution of alpha-aminoboronic esters by diastereoselective crystallization with pinanediols. Confirmation by x-ray analysis", Tetrahedron: Asymmetry (1997) 8(9):1435-1440.

Bush et al., "Minireview: Updated Functional Classification of beta-Lactamases," Antimicrob Agents Chemo. (2010) 54(3):969-976.

Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.

Coppa et al., "A Facile, Convenient and Selective Homolytic Carbamolylation of Heteroaromatic Bases", Heterocycles (1993) 36(12):2687-2696.

Coutts et al., "Two Efficient Methods for the Cleavage of Pinanediol Boronate Esters Yielding the Free Boronic Acids", Tetrahedron Ltt. (1994) 35(29):5109-5112.

Darses et al., "Potassium Organotrifluoroborates: New Perspectives in organic Synthesis", Chem Rev. (2008) 108:288-325.

Davoli et al., "Enantioselective total synthesis of (-)-microcarpalide", Tetrahedron (2005) 61:4427-4436.

Di Gioia et al., "Optically Pure N-Hydroxy-O-triisopropylsilyl-alpha-L-amino Acid Methyl Esters from AICI3-Assisted Ring Opening of Chiral Oxaziridines by Nitrogen Containing Nucleophiles", J Org Chem. (2005) 70(25):10494-10501.

Endo et al., "Chemoselective Suzuki coupling of diborylmethane for facile synthesis of benzylboronates", Org Lett. (2011) 13(13):3368-3371.

Eidam et al., "Design, synthesis, crystal structures and antimicrobial activity of sulfonamide boronic acids as beta-lactamase inhibitors", J Med Chem. (2010) 53(21):7852-7863.

Eissenstat et al., "Aminoalkylindoles: Structure-Activity Relationships of Novel Cannabinoid Mimetics", J Med Chem. (1995) 38(16):3094-3105.

El Nezhawy et al., "Synthesis and antioxidant activity of some thiazolidin-4-one derivatives", Springer; Chemical Monthly/Monatshefte für Chemie (2009) 140(5):531-539.

Fan, et al. (2009): STN International HCAPLUS database, Columbus (OH), accession No. 2009: 425839; 6 pages.

Farquhar et al., "Intensely potent doxorubicin analogues: structure—activity relationship", J. Med. Chem. (1998) 41(6):965-972.

Ghosh et al., "Enantioselective total synthesis of (+)-largazole, a potent inhibitor of histone deacetylase", Org Lett. (2008) 10(17):3907-3909.

Giroux, A., "Synthesis of benzylic boronates via palladium-catalyzed cross-coupling reaction of bis(pinacolato)diboron with benzylic halides", Tetrahedron Lett. (2003) 44:233-235.

Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.

Hama et al., "Palladium-Catalyzed alpha-Arylation of Zinc Enolates of Esters: Reaction Conditions and Substrate Scope", J Org Chem. (2013) 78(17):8250-8266.

Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.

Inglis et al., "Observations on the Deprotection of Pinanediol andP-pinacol Boronate Esters via Fluorinated Intermediates", J Org Chem. (2010) 75(2):468-471.

Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.

(56) References Cited

OTHER PUBLICATIONS

Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]- boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.
Jiang et al., "A Practical Synthesis of Cefcapene Pivoxil", Synthesis (2012) 44:207-214.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", (1993) 22(5):845-848.
Kint et al., "New-found fundamentals of bacterial persistance", Trends Microbiol. (2012) 20(12):577-585.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kumar et al., "Synthesis of intermediates for the lactone moiety of mevinic acids via tellurium chemistry", J. Org. Chem., (1994) 59(17):4760-4764.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Laitar et al., "Catalytic diboration of aldehydes via insertion into the copper-boron bond", J Am Chem Soc. (2006) 128(34):11036-11037.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Liu et al., "Selective Protein tyrosine phosphatase 1B inhibitors: Targeting the second phosphotyrosine binding site with non-carboxylic acid-containing ligands", J Med Chem. (2003) 46(16):3437-3440.
Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.

Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Synthesis of a (Beta-acetamido-alpha-acetoxyethyl) boronic ester via azido boronic esters", J Organomet Chem. (2008) 693:2258-2262.
Meanwell, "Synopsis of some recent tactical application of bioisosteres in drug design", J. Med. Chem. (2011) 54:2529-2591.
Micalizio et al., "A Boronic Ester Annulation Strategy for Diversity-Oriented Organic Synthesis", Angew Chem Int Ed Engl. (2002) 41(1):152-154.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205 Epub Nov. 7, 2007.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nordmann et al., How to Detect NDM-1 Producers, J. Clin. Micro. (2011) 49:718-721.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Paterson et al., "Extended-Spectrum beta-Lactamases: a Clinical Update", Clin Microbiol Rev. (2005) 18(4):657-686.
Perez et al., "Why are we afraid of Acinetobacter baumannii?", Expert Rev Anti Infect Ther. (2008) 6(3):269-71.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Powell et al., "Compendium of excipients for parenteral formulations", PDA J Pharm Sci Technol. (1998) 52(5):238-311.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Rodriguez-Martinez et al., "VIM-19, a Metallo-beta-lactamase with increased Carbapenemase Activity from *Escherichia coli* and *Klebsiella pneumoniae*", Antimicro Agents Chemother. (2010) 54(1):471-476.
Sawyer et al., "Physical properties and synthetic utility of a-alkoxyorganolithium species as studied through ligand selectivity in tin-lithium exchange", J. Am. Chem. Soc. (1988) 110:842-853.
Selander et al., "Palladium-catalyzed allylic C-OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singh et al., "Assymmetric Homologation of Boronic Esters Bearing Azido and Silyloxy Substituents", J Org Chem (2000) 65(20):6650-6653 and Erratum, J Org Chem. (2001) 66(22):7560.
Sliwka et al., "Synthetic Sulfur Carotenoids II: Optically Active Carotenoid Thiols", Tetrahedron: Asymmetry (1993) 4(3):361-368.

(56) References Cited

OTHER PUBLICATIONS

Solladié et al., "First Stereocontrolled Synthesis of the (3S,5R,7R,10R,11R)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C—H insertion", Tetrahedron (2002) 58:6545-6554.
Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
Vasil'Ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Waley, Stephen G., "A quick method for the determination of inhibition constants", Biochem J. (1982) 205(3):631-633.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Wohlrab et al., "Total synthesis of plusbacin A3: a depsipeptide antibiotic active against vancomycin-resistant bacteria", J. Am. Chem. Soc. (2007) 129:4175-4177.
Xia et al., "Synthesis and SAR of novel benzoxaboroles as a new class of beta-lactamase inhibitors", Bioorg Med Chem Lett. (2011) 21:2533-2536.
Yamamoto et al., "Iridium-catalyzed hydroboration of alkenes with pinacolborane", Tetrahedron (2004) 60:10695-10700.
Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.
Yuen et al., "Deprotection of pinacolyl boronate esters via hydrolysis of intermediate potassium trifluoroborates", Tetrahed Lttr. (2005)46(46):7899-7903.
International Search Report and Written Opinion dated Sep. 14, 2011 for International Patent Application No. PCT/US2011/046957, filed Aug. 8, 2011.
International Search Report and Written Opinion dated Nov. 5, 2012 for International Patent Application No. PCT/US2012/053233, filed Aug. 30, 2012.
International Search Report and Written Opinion dated May 9, 2013 for International Patent Application No. PCT/US2013/025621, filed Feb. 11, 2013.
International Search Report and Written Opinion dated Aug. 29, 2013 for International Application No. PCT/US2013/044377, filed Jun. 5, 2013.
International Search Report and Written Opinion dated Mar. 12, 2014 for International Patent Application No. PCT/US2014/010106, filed Jan. 2, 2014.
International Search Report and Written Opinion dated Mar. 12, 2014 for International Patent Application No. PCT/US2014/010107, filed Jan. 2, 2014.
U.S. Office Action, mailed Aug. 20, 2013, in co-pending/related U.S. Appl. No. 13/205,112.
U.S. Office Action, mailed Apr. 1, 2014, in co-pending/related U.S. Appl. No. 13/898,959.
Chemicalland21.com. "Meglumine", Jun. 7, 2011. Downloaded from </www.chemicalland21.com/lifescience/phar/N-METHYL-D-GLUCAMINE.htm>.
International Preliminary Report on Patentability dated Nov. 19, 2014 for International Patent Application No. PCT/US2014/010107, filed Jan. 2, 2014.
U.S. Office Action mailed Oct. 3, 2014 in U.S. Appl. No. 14/146,643.
American Chemical Society. STN Chemical Database Registry RN: 1226917; Jun. 2010; 2 pages
CAS Registry Nos. 69190-59-6 (2-(bis(phenylthio)methyl)-4,4,5,5-tetramethyl-1,3,2- dioxaborolane) and 69190-60-9 (2-(bis(phenylthio)methyl)-1,3,2-dioxaborinane) Scheme 18 (2015); 2 pages.
CAS Registry No. 105892-95-3 Boronic acid [1-(phenylsulfonyl)heptyl]-, dimethyl ester (2015); 2 pages.
de Meijere A. [Ed], Science of Synthesis—vol. 24; "Three Carbon-Heteroatom Bonds: Ketene Acetals and Yne-X Compounds", TOC 46 pages.
Drawz et al., "Three Decades of beta-Lactamase Inhibitors", Clin Microbiol Reviews (Jan. 2010) 23(1):160-201.
Gorovoy et al., "Boron-Containing Peptidomimetics—A Novel Class of Selective Anti-tubercular Drugs", Chem Biol Drug Des. (Jan. 2013) 81:408-413.
Kumar et al., "Development of Practical Methodologies for the Synthesis of Functionalized Benzoboroxoles", Tetrahedron Lett. (Aug. 25, 2010) 51(34):4482-4485.
Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131(51):18234-18235.
Lima et al., "Bioisosterism: A Useful Strategy for Molecular Modification and Drug Design", Curr Med Chem. (2005) 12:23-49.
Matteson et al., "Glass-Catalyzed Conversion of Boronic Esters of Asymmetric Diols to Diol Sulfites and Amine Complexes of Boron Halides", Oranometallics (2001) 20:2920-2923 & supporting Information (9 pages).
Matteson et al., "Cesium Alkyltrifluoroborates from Asymmetric Boronic Esters" Synlett (Jul. 2006) 20:3501-3502.
Mendoza et al., "Bis(phenylthio)methaneboronic Esters as Sources of Carbanions and Ketene Thioacetals", J Org Chem. (1979) 44(8):1352-1354.
Patani et al., "Bioisosterism: A Rational Approach in Drug Design", Chem Rev. (1996) 96:3147-3176.
Webb et al., "Metal catalysed hydroboration of vinyl sulfides, sulfoxides, sulfones, and sulfonates", J Mol Cat A: Chem. (2007) 275:91-100.

\* cited by examiner

BORONIC ACID DERIVATIVES AND THERAPEUTIC USES THEREOF

CROSS-REFERENCE TO RELATED APPLICATIONS

This application claims the benefit of U.S. Provisional Application No. 61/749,204, filed Jan. 4, 2013, which is incorporated herein by reference in its entirety.

BACKGROUND

1. Field of the Invention

The present invention relates to the fields of chemistry and medicine. More particularly, the present invention relates to boronic acid antimicrobial compounds, compositions, their preparation, and their use as therapeutic agents.

2. Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of antibacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

The zinc-dependent class B metallo-β-lactamases are represented mainly by the VIM, IMP, and NDM types. IMP and VIM-producing *K. pneumonia* were first observed in 1990s in Japan and 2001 in Southern Europe, respectively. IMP-positive strains remain frequent in Japan and have also caused hospital outbreaks in China and Australia. However dissemination of IMP-producing Enterobacteriaceae in the rest of the word appears to be somewhat limited. VIM-producing enterobacteria can be frequently isolated in Mediterranean countries, reaching epidemic proportions in Greece. Isolation of VIM-producing strains remains low in Northern Europe and in the United States. In stark contrast, a characteristic of NDM-producing *K. pneumonia* isolates has been their rapid dissemination from their epicenter, the Indian subcontinent, to Western Europe, North America, Australia and Far East. Moreover, NDM genes have spread rapidly to various species other than *K. pneumonia*.

The plasmid-expressed class D carbapenemases belong to OXA-48 type. OXA-48 producing *K. pneumonia* was first detected in Turkey, in 2001. The Middle East and North Africa remain the main centers of infection. However, recent isolation of OXA-48-type producing organisms in India, Senegal and Argentina suggest the possibility of a global expansion. Isolation of OXA-48 in bacteria other than *K. pneumonia* underlines the spreading potential of OXA-48.

Treatment of strains producing any of these carbapenemases with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved β-lactamase inhibitors.

SUMMARY

Some embodiments disclosed herein include a compound having the structure of formula I:

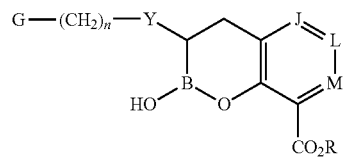

or pharmaceutically acceptable salt thereof, wherein:

Y is selected from the group consisting of —S—, —O—, —CH$_2$—, and —NH—;

n is 0-3;

G is selected from the group consisting of —C(O)NR$^1$R$^2$; —C(O)NR$^1$OR$^2$; —NR$^1$C(O)R$^2$; —NR$^1$C(O)NR$^2$R$^3$; —NR$^1$C(O)OR$^2$; —NR$^1$S(O)$_2$R$^2$; —NR$^1$S(O)$_2$NR$^2$R$^3$; —C(=NR$^1$)R$^2$; —C(=NR$^1$)NR$^2$R$^3$; —NR$^1$CR$^2$(=NR$^3$); —NR$^1$C(=NR$^2$)NR$^3$R$^4$; aryl optionally substituted with 0-2 substituents selected from the group consisting of C$_{1-4}$ alkyl, —OR$^1$, —NR$^1$R$^2$, halogen, —C(O)NR$^1$R$^2$, and —NR$^1$C(O)R$^2$; heteroaryl optionally substituted with 0-2 substituents selected from the group consisting of C$_{1-4}$ alkyl, —OR$^1$, —NR$^1$R$^2$, halogen, —C(O)NR$^1$R$^2$, and —NR$^1$C(O)R$^2$; and heterocyclyl optionally substituted with 0-2 substituents selected from the group consisting of C$_{1-4}$ alkyl, —OR$^1$, —NR$^1$R$^2$, halogen, —C(O)NR$^1$R$^2$, and —NR$^1$C(O)R$^2$;

J, L, and M are each independently selected from the group consisting of CR$^7$ and N;

R is selected from a group consisting of —H, —C$_{1-9}$alkyl, —CR$^5$R$^6$OC(O)C$_{1-9}$alkyl, —CR$^5$R$^6$OC(O)OC$_{1-9}$alkyl, and

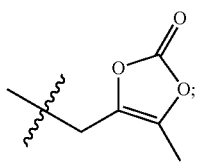 [SMILES: *Cc1oc(=O)oc1C]

R$^1$, R$^2$, R$^3$, R$^4$, R$^5$ and R$^6$ are each independently selected from —H and —C$_{1-4}$alkyl; and R$^7$ is selected from the group consisting of —H, —C$_{1-4}$ alkyl, —OH, —OC$_{1-4}$alkyl, and halogen.

Other embodiments disclosed herein include a pharmaceutical composition comprising a therapeutically effective amount of a compound disclosed herein and a pharmaceutically acceptable excipient.

Other embodiments disclosed herein include a method of treating or preventing a bacterial infection, comprising administering to a subject in need thereof a compound disclosed herein.

DETAILED DESCRIPTION

In some embodiments, compounds that contain a boronic acid moiety are provided that act as antimicrobial agents and/or as potentiators of antimicrobial agents Various embodiments of these compounds include compounds having the structures of Formula I as described above or pharmaceutically acceptable salts thereof.

Some embodiments of compounds of Formula (I) or their pharmaceutically acceptable salts have the following stereochemistry as shown in the structure of formula (Ia):

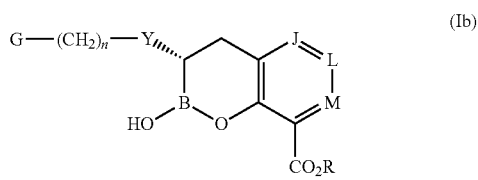

Some embodiments of compounds of Formula (I) or their pharmaceutically acceptable salts have the following stereochemistry as shown in the structure of formula (Ib):

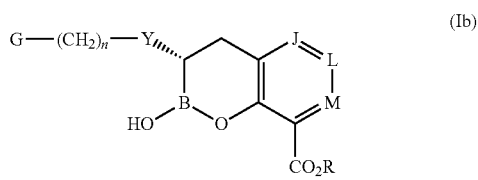

In some embodiments, n is 0 or 1.

In some embodiments, Y is O or S; G is selected from the group consisting of phenyl, imidazole, pyrazole, triazole, tetrazole, thiazole, thiadiazole, oxazole, oxadiazole, isoxazole, isothiazole, pyridine, pyrazine, pyrimidine, pyridazine, and pyrazine, each optionally substituted by 0-2 substituents selected from the group consisting of —OR$^1$, —NR$^1$R$^2$, halogen, —C(O)NR$^1$R$^2$, and —NR$^1$C(O)R$^2$; and J, L and M are CR$^7$.

In some such embodiments, n is 0. In some such embodiments, G is thiadiazole. In other embodiments, G is thiadiazole optionally substituted with —NR$^1$R$^2$ or —NR$^1$C(O)R$^2$, wherein R$^1$ and R$^2$ are independently H or —C$_{1-4}$alkyl. In other embodiments, G is triazole optionally substituted with NR$^1$R$^2$, wherein R$^1$ and R$^2$ are independently H or —C$_{1-4}$ alkyl. In other embodiments, G is tetrazole optionally substituted with methyl. In still other embodiments, G is pyridine, thiazole, or phenyl.

In some embodiments, Y is S; n is 1 or 2; G is —C(O)NR$^1$R$^2$ or —C(=NR$^1$)R$^2$; and J, L, and M are CR$^7$. In some such embodiments, R$^7$ is H. In other embodiments, R$^1$ is H and R$^2$ is H.

Some specific embodiments of the compounds described herein have the following structures:

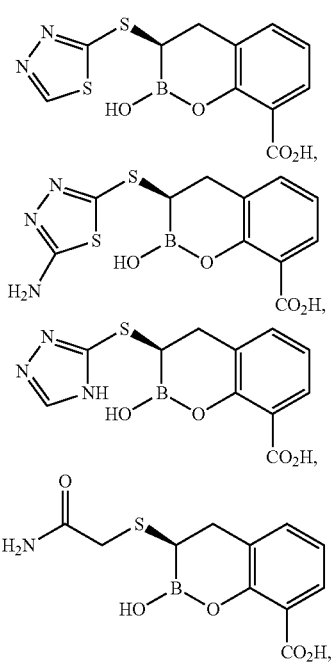

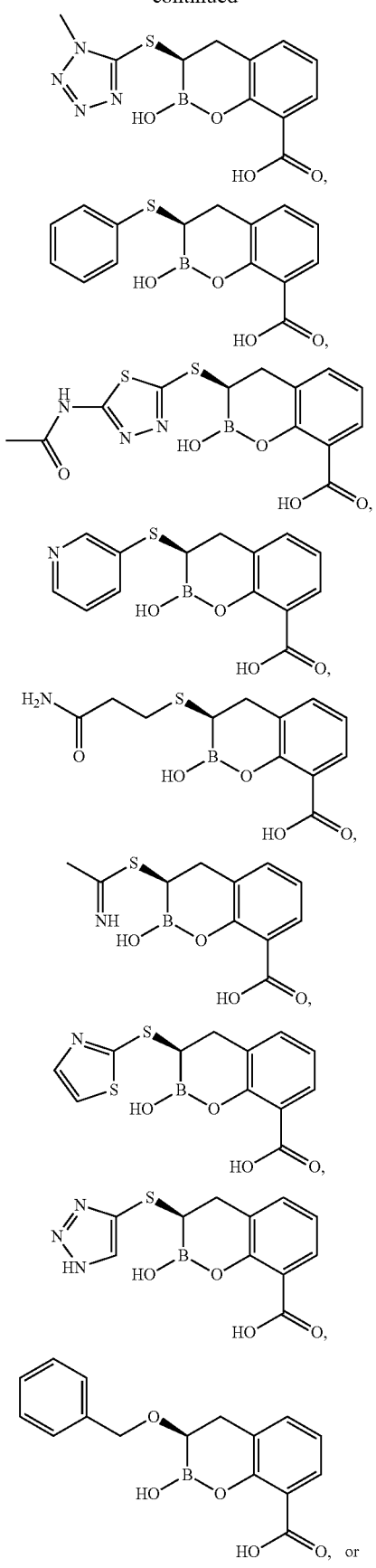

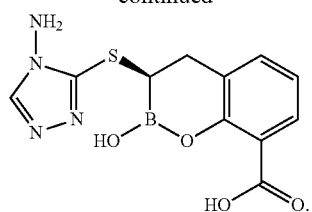

Some embodiments of any of the compounds described above include prodrugs (e.g., prodrug esters), metabolites, stereoisomers, hydrates, solvates, polymorphs, and pharmaceutically acceptable salts of those compounds.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As shown below, the compounds disclosed herein may exist in cyclic form as cyclic boronate monoesters as formula I or in acyclic form as boronic acids as formula I.1 (*Biochemistry*, 2000, 39, 5312-21), or may exist as a mixture of the two forms depending on the medium. Such compounds or mixture of compounds are considered within the scope of the structures depicted, though such structural forms are not explicitly represented herein.

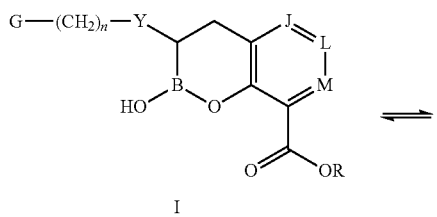
I

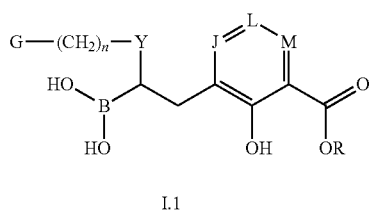
I.1

DEFINITIONS

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group of the compounds may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group of the compounds may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations.

Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.
A "cyanato" group refers to an "—OCN" group.
An "isocyanato" group refers to a "—NCO" group.
A "thiocyanato" group refers to a "—SCN" group.
An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and Rb are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, a$C_{6-10}$ryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups for oxygen atoms are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)). Handling of protecting and/or sterodirecting groups specific to boronic acid derivatives is described in a recent review of chemistry of boronic acids: D. G. Hall (Ed.), Boronic Acids. Preparation and Application in Organic Synthesis and Medicine, Wiley VCH (2005) and in earlier reviews: Matteson, D. S. (1988). Asymmetric synthesis with boronic esters. Accounts of Chemical Research, 21(8), 294-300, and Matteson, D. S. (1989). Tetrahedron, 45(7), 1859-1885), all of which are incorporated herein by reference in their entirety. The latter review articles also describe methodology for stereoselective insertion of halomethine functionality next to the boronate which is employed in the synthetic schemes below.

In addition to standard acid catalyzed deprotection, special methods for removal of boronic acid protecting and/or sterodirecting groups methods using fluorides (Yuen, A. K. L., & Hutton, C. A. (2005). Tetrahedron Letters, 46(46), 7899-7903—incorporated herein by reference in its entirety) or periodate oxidation (Coutts, S. J., et al. (1994). Tetrahedron Letters, 35(29), 5109-5112—incorporated herein by reference in its entirety) can also be employed in preparations of the compounds disclosed herein.

In strategies employing pinanediol or other diol-based chiral auxiliaries for stereospecific introduction of new chiral centers, the early stages of chemistry on boronic intermediates can be performed on chiral boronate esters or alternatively nonchiral borate/boronate intermediates can be used in early stages followed by transesterification with chiral diols prior to the step where stereoselection is required.

Synthesis of Compounds of Formula I

The following example schemes are provided for the guidance of the reader, and collectively represent an example method for making the compounds encompassed herein. Furthermore, other methods for preparing compounds described herein will be readily apparent to the person of ordinary skill in the art in light of the following reaction schemes and examples. Unless otherwise indicated, all variables are as defined above.

Compounds of formula Ia where R is H can be prepared as depicted in scheme 1 from key intermediates of formula III, which may be assembled by known reactions (Boronic Acids: Preparations and Applications in Organic Synthesis, Medicine and Materials, D. G. Hall, ed., Wiley-VCH, Weinheim, 2011).

Scheme 1

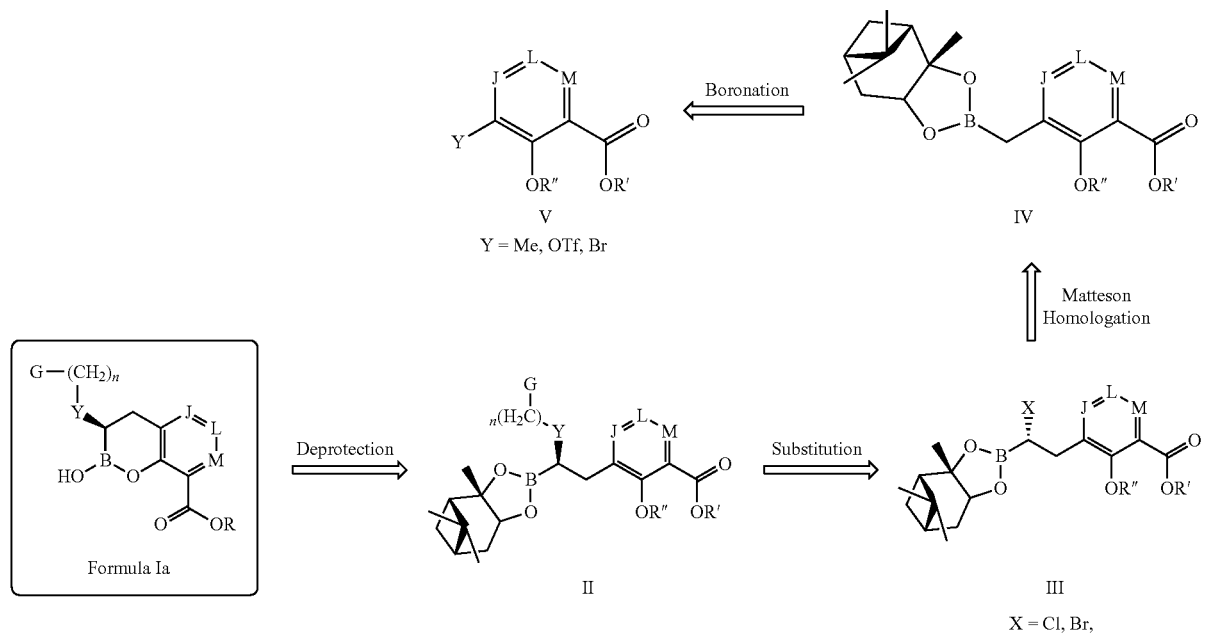

Such key intermediates of formula III where X=Cl and R' and R" are alkyl groups may be prepared by earlier described methods (WO09064414, WO10130708). In an alternate sequence, compounds of formula III where X=Cl and R' is Boc and R" is t-Butyl or R' and R" are protected together as isopropylidine or any other groups protected separately or together in cyclic form may be made from compounds of formula IV via homologation to give chloromethylene addition product with good stereocontrol by Matteson reaction conditions (WO0946098). Compounds of formula III where X is bromo may be made analogously to the chloro compounds of Scheme 1, utilizing dibromomethane (*J. Am. Chem. Soc.* 1990, 112, 3964-969). The halo derivatives of formula III where X is Cl or Br undergo stereospecific substitution to form thioethers (WO 04064755), ethers (WO 12067664), amines (*J. Organomet. Chem.* 1979, 170, 259-64) or acetates (*Tetrahedron* 2005, 61, 4427-4536), to give compounds of formula II. In an alternate approach, compounds of formula II where Y is S can be made via a thiol intermediate by alkylation or arylation to introduce various G groups. Such compounds may also be made via alkyl or thiomethylene boronate esters by reaction with substituted benzyl halides (U.S. Pat. No. 6,586,615).

Matteson reaction precursors of formula IV may be made by palladium mediated coupling of pinanediol diboronate from corresponding appropriately protected benzyl alcohols (*J. Am. Chem. Soc.* 2011, 133, 409-411) or benzyl bromides of V (*Tetrahedron Letters* 2003, 44, 233-235; *J. Am. Chem. Soc.*, 2010, 132, 11825-11827). The compounds of formula V may be achieved by means of several earlier known methods (WO0458679) with conventional protecting groups, such as those described in *Protective Groups in Organic Chemistry* (ed. J. F. W. McOmie, Plenum, 1973); and *Protecting Groups in Organic Synthesis* P. G. M. Wutts, T. W. Green, Wiley, New York, 1999) from commercially available salicylic acid derivatives. Compounds of formula V where X is methyl can be readily transformed to corresponding benzyl bromides (*Bioorg. Med. Chem. Lett.* 1999, 9, 34-346) for boronation reaction to give IV.

Simultaneous deprotection of pinane ester and salicylic acid protective groups of compounds of formula II can be achieved by heating with dilute HCl, affording the desired compounds of structure I. This transformation may also be achieved by treatment with $BCl_3$ or $BBr_3$ (WO09064414). Alternatively, the deprotection may be attained via transesterification with isobutyl boronic acid in presence of dilute acid (WO09064413) or via other known methods (*J. Org. Chem.* (2010), 75, 468-471).

Compounds of formula Ib may be made following the sequence described above via (−)-pinanediol substituted intermediate of IV.

Synthesis of Prodrugs

Compounds of formula I where the R is a prodrug moiety may be synthesized by a variety of known methods of different carboxylic acid prodrugs (*Prodrugs: Challenges and Rewards*, V. J. Stella, et al., ed., Springer, New York, 2007). These prodrugs include but are not limited to substituted or non-substituted alkyl esters, (acyloxy)alkyl (*Synthesis* 2012, 44, 207), [(alkoxycarbonyl)oxy]methyl esters (WO10097675), or (oxodioxolyl)methyl esters (*J. Med. Chem.* 1996, 39, 323-338). Such prodrugs can be made from compounds of formula I where R=H by treatment with acid or in neutral conditions (e.g., carbodiimide coupling) in the presence of alcohols (ROH) or via base promoted esterification with RX where X is a leaving group in the presence of an appropriate base. Alternatively, boronate esters of formula VI or corresponding tetrafluoroborates (*Chem. Rev.* 2008, 108, 288-325) may be also utilized for introduction of prodrugs and convert them to final prodrugs (Scheme 2). Such carboxylic acids (VI) can be made from compounds of formula II by selective deprotection of OR'. The prodrug group may also be introduced earlier in the sequence in compounds of formula V where R' is R. Such sequence where prodrug is introduced in earlier intermediates is only feasible when the ester is stable under the final deprotection conditions to remove the phenol protective group and boronate ester group.

Scheme 2

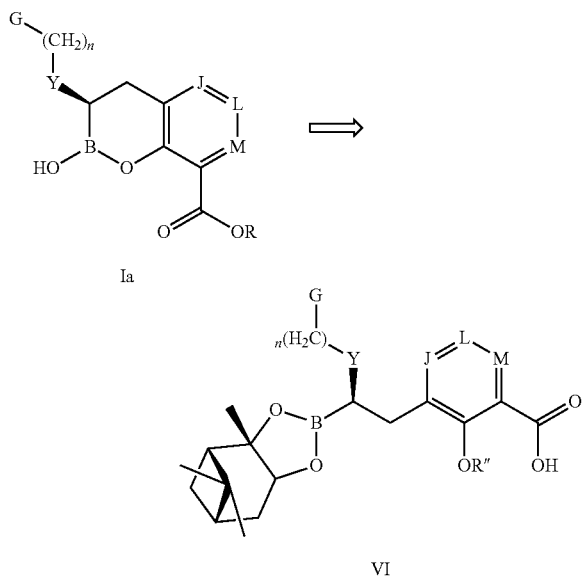

Ia

VI

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Methods of Treatment

Some embodiments of the present invention include methods of treating bacterial infections with the compounds and compositions comprising the compounds described herein. Some methods include administering a compound, composition, pharmaceutical composition described herein to a subject in need thereof. In some embodiments, a subject can be an animal, e.g., a mammal (including a human). In some embodiments, the bacterial infection comprises a bacteria described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Examples of additional medicaments include an antibacterial agent, antifungal agent, an antiviral agent, an anti-inflammatory agent and an anti-allergic agent.

Preferred embodiments include combinations of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam and Carumonam.

Preferred embodiments include β-lactams such as Ceftazidime, Biapenem, Doripenem, Ertapenem, Imipenem, Meropenem and Panipenem.

Additional preferred embodiments include β-lactams such as Aztreonam, Tigemonam, and Carumonam.

Some embodiments include a combination of the compounds, compositions and/or pharmaceutical compositions described herein with an additional agent, wherein the additional agent comprises a monobactam. Examples of monobactams include aztreonam, tigemonam, nocardicin A, carumonam, and tabtoxin. In some such embodiments, the compound, composition and/or pharmaceutical composition comprises a class A, C, or D beta-lactamase inhibitor. Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises a class B beta lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises one or more agents that include a class A, B, C, or D beta lactamase inhibitor. Some embodiments include co-administering the compound, composition or pharmaceutical composition described herein with the one or more additional agents.

Indications

The compounds and compositions comprising the compounds described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

The following examples will further describe the present invention, and are used for the purposes of illustration only, and should not be considered as limiting.

EXAMPLES

Example 1

(R)-3-(1,3,4-thiadiazol-2-ylthio)-2-hydroxy-3,4-dihydro-2H-benzo[e][1,2]oxaborinine-8-carboxylic acid (1)

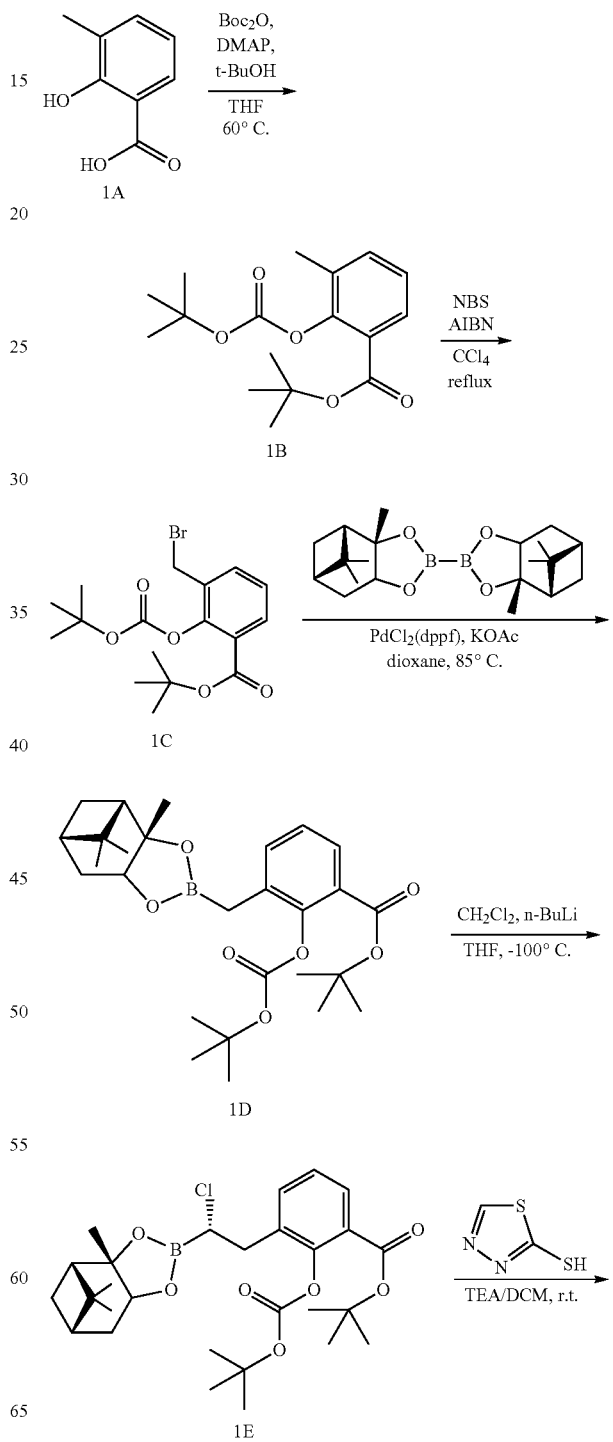

-continued

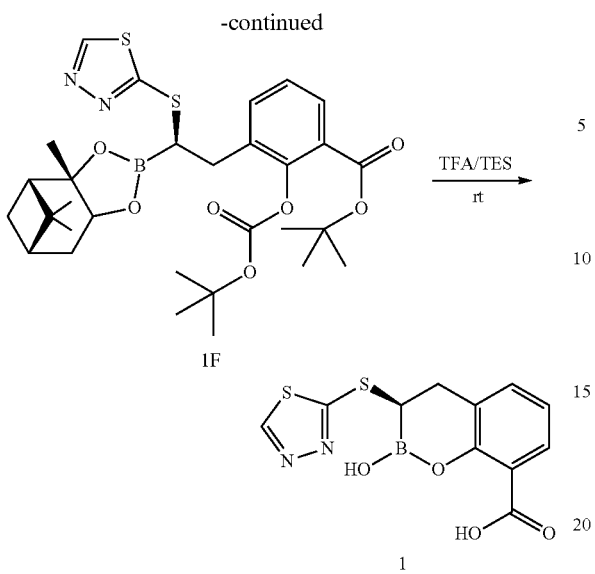

1F

1

Step 1: Synthesis of Compound 1B

To the solution of compound 1A (100 g, 0.657 mol) in THF (400 mL) was added Boc₂O (573 g, 2.63 mol), DMAP (24 g, 0.197 mol) and ᵗBuOH (800 mL). The resulting solution was stirred at 60° C. for 6 hours before it was concentrated in vacuo. The residue was purified by flash column chromatography (ethyl acetate/hexanes, v/v, 1/200~1/100) to give the titled compound 1B (85.9 g, 42.5% yield) as colorless oil.

Step 2: Synthesis of Compound 1C

To the solution of compound 1B (44.3 g, 144 mmol) and NBS (28.1 g, 158 mmol) in CCl₄ (400 mL) was added BPO (3.5 g, 14.4 mmol). The resulting mixture was refluxed at 80° C. for 15 hours. The solid was filtered off and the filtrate was concentrated in vacuo. The residue was recrystallized with hexanes to afford the titled compound 1C (32.0 g, 57.6% yield) as white solid.

Step 3: Synthesis of Compound 1D

The mixture of compound 1C (47.5 g, 123 mmol), bis(pinanediolato)diboron (39.9 g, 112 mmol), KOAc (32.9 g, 336 mmol) and PdCl₂(dppf) (4.5 g, 5.6 mmol) in dioxane (500 mL) was degassed for three times and flushed with nitrogen. The mixture was stirred at 95° C. for 8 hours. After concentrated to dryness, the residue was purified by column chromatography (ethyl acetate/hexanes, v/v, 1/200~1/100) to give the titled compound 1D (40 g, 59% yield) as slightly yellow oil.

Step 4: Synthesis of Compound 1E

To a solution of CH₂Cl₂ (4.2 mL, 65.8 mmol) in THF (160 mL) at −100° C. was added 2.5 M n-butyl lithium in hexane (18.4 mL, 46.0 mmol) slowly under nitrogen and down the inside wall of the flask, maintaining the temperature below −90° C. The reaction mixture was stirred at −100° C. for another 30 minutes before the addition of Compound 1D from step 3 (16.0 g, 32.9 mmol) in THF (30 mL) at −90° C. and then the reaction was allowed to warm to room temperature where it was stirred for 16 h. The reaction was concentrated in vacuo directly to dryness and then chromatographed (100% hexane-20% EtOAc-hexane) to obtain the titled compound 1E (15.0 g, 85% yield) as slightly yellow oil.

Step 5: Synthesis of 1F

To the solution of compound 1E (113 mg, 0.21 mmol) and 2-mercapto-1,3,4-thiadiazole (32 mg, 0.27 mmol) in DCM (1.5 mL) was added triethylamine (42 mg, 0.42 mmol) at room temperature. After stirring for 2 hours, the reaction diluted with DCM and washed with dilute aqueous HCl and water. After concentration, the titled compound 1F (132 mg) was obtained as slightly yellow oil, which was used for next step without further purification.

Step 6: Synthesis of (R)-3-(1,3,4-thiadiazol-2-ylthio)-2-hydroxy-3,4-dihydro-2H-benzo[e][1,2]oxaborinine-8-carboxylic acid (1)

To the mixture of TFA (6 mL) and triethylsilane (1 mL) was added compound 1F (127 mg, crude). The resulting solution was stirred at room temperature for 1 hour before it was concentrated to dryness. The residue purified by reverse-phase prep-HPLC to afford 1 (43.2 mg) as white solid.

$^1$H NMR (400 MHz, CD₃OD) δ 9.28 (s, 1H), 7.76 (d, 1H, J=8.0 Hz), 7.35 (d, 1H, J=7.6 Hz), 6.94 (dd, 1H, J=8.0, 8.0 Hz), 3.80-3.90 (m, 1H), 3.25-3.30 (m, 1H), 3.08 (dd, 1H, J=2.8, 16 Hz).

MS calcd for (C₁₁H₉BN₂O₄S₂): 308

MS (ESI, positive) found: (M+1): 309

MS (ESI, negative) found: (M+H2O-1): 325

Example 2

(R)-3-(4H-1,2,4-triazol-3-ylthio)-2-hydroxy-3,4-dihydro-2H-benzo[e][1,2]oxaborinine-8-carboxylic acid (2)

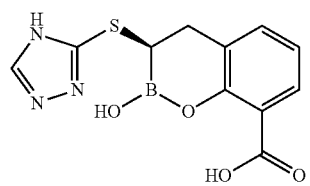

2

(R)-3-(4H-1,2,4-triazol-3-ylthio)-2-hydroxy-3,4-dihydro-2H-benzo[e][1,2]oxaborinine-8-carboxylic acid (2) was prepared following similar procedure described in example 1 (steps 1-6) replacing 2-mercapto-1,3,4-thiadiazole in step 5 with 4H-1,2,4-triazole-3-thiol $^1$H NMR (400 MHz, CD₃OD) δ 8.61 (bs, 1H), 7.73 (d, 1H, J=7.6 Hz), 7.31 (d, 1H, J=7.6 Hz), 6.91 (dd, 1H, J=7.6, 7.6 Hz), 3.82 (s, 1H), 3.22 (dd, 1H, J=5.2, 15.6 Hz), 2.98 (dd, 1H, J=2.8, 15.6 Hz).

MS calcd for (C₁₁H₁₀BN₃O₄S): 291

MS (ESI, positive) found: (M+1): 292

MS (ESI, negative) found: (M−1): 290

Example 3

(R)-3-(2-amino-2-oxoethylthio)-2-hydroxy-3,4-dihydro-2H-benzo[e][1,2]oxaborinine-8-carboxylic acid (3)

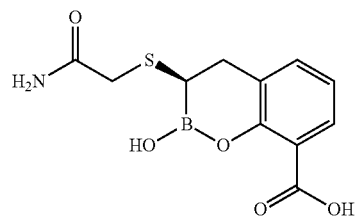

(R)-3-(2-amino-2-oxoethylthio)-2-hydroxy-3,4-dihydro-2H-benzo[e][1,2]oxaborinine-8-carboxylic acid (3) was prepared following similar procedure described in example 1 (steps 1-6) replacing 2-mercapto-1,3,4-thiadiazole in step 5 with 2-mercaptoacetamide.

$^1$H NMR (400 MHz, CD$_3$OD) δ 7.82 (dd, 1H, J=1.6, 8.0 Hz), 7.30 (m, 1H), 6.90 (dd, 1H, J=7.6, 8.0 Hz), 3.35 (d, 1H, J=13.6 Hz), 3.35 (d, 1H, J=14.0 Hz), 3.07 (dd, 1H, J=5.2, 15.6 Hz), 2.75 (dd, 1H, J=7.6, 15.6 Hz), 2.53 (dd, 1H, J=5.2, 7.6 Hz).

MS calcd for (C$_{11}$H$_{12}$BNO$_5$S): 281
MS (ESI, positive) found: (M+1): 282
MS (ESI, negative) found: (M−1): 280

Example 4

(R)-3-(5-amino-1,3,4-thiadiazol-2-ylthio)-2-hydroxy-3,4-dihydro-2H-benzo[e][1,2]oxaborinine-8-carboxylic acid (4)

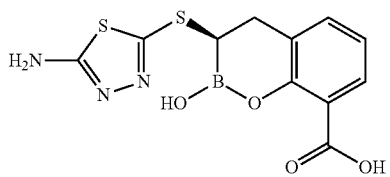

(R)-3-(5-amino-1,3,4-thiadiazol-2-ylthio)-2-hydroxy-3,4-dihydro-2H-benzo[e][1,2]oxaborinine-8-carboxylic acid (4) was prepared following similar procedure described in example 1 (steps 1-6) replacing 2-mercapto-1,3,4-thiadiazole in step 5 with 5-amino-1,3,4-thiadiazole-2-thiol.

$^1$H NMR (400 MHz, CD$_3$OD) δ 7.80 (d, 1H, J=8.0 Hz), 7.34 (d, 1H, J=7.6 Hz), 6.96 (dd, 1H, J=7.6, 7.6 Hz), 3.69 (S, 1H), 3.23 (dd, 1H, J=5.6, 16 Hz), 3.02 (d, 1H, J=16 Hz).

MS calcd for (C$_{11}$H$_{10}$BN$_3$O$_4$S$_2$): 323
MS (ESI, positive) found: (M+1): 324
MS (ESI, negative) found: (M−1): 322

Example 5

(R)-2-hydroxy-3-(1-1H-tetrazol-5-ylthio)-3,4-dihydro-2H-benzo[e][1,2]oxaborinine-8-carboxylic acid (5)

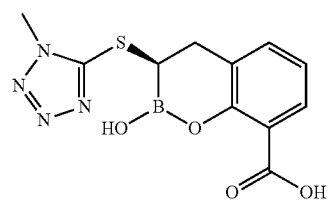

$^1$H NMR (400 MHz, CD$_3$OD) δ 7.70-7.78 (m, 1H), 7.22-7.33 (m, 1H), 6.78-6.90 (m, 1H), 3.82-3.88 (m, 4H), 3.08-3.20 (m, 2H).

MS calcd for (C$_{11}$H$_{11}$BN$_4$O$_4$S): 306
MS (ESI, positive) found: (M+1): 307
MS (ESI, negative) found: (M+H2O-1): 323

Example 6

(R)-2-hydroxy-3-(phenylthio)-3,4-dihydro-2H-benzo[e][1,2]oxaborinine-8-carboxylic acid (6)

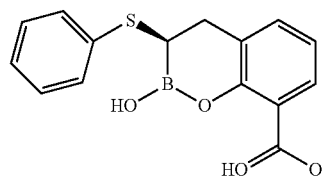

$^1$H NMR (400 MHz, CD$_3$OD) δ 7.70-7.81 (m, 1H), 7.07-7.42 (m, 4H), 6.75-6.95 (m, 2H), 2.72-3.24 (m, 3H).

MS calcd for (C$_{15}$H$_{13}$BO$_4$S): 300
MS (ESI, positive) found: (M+1): 301
MS (ESI, negative) found: (M+H2O-1): 317

Example 7

(R)-3-(5-acetamido-1,3,4-thiadiazol-2-ylthio)-2-hydroxy-3,4-dihydro-2H-benzo[e][1,2]oxaborinine-8-carboxylic acid (7)

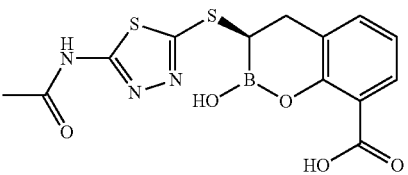

$^1$H NMR (400 MHz, CD$_3$OD) δ 7.77 (d, 1H, J=7.6 Hz), 7.34 (d, 1H, J=7.6 Hz), 6.94 (dd, 1H, J=7.6, 7.6 Hz), 3.76 (s, 1H), 3.03-3.30 (m, 2H), 2.20 (s, 3H).

MS calcd for (C$_{13}$H$_{12}$BN$_3$O$_5$S$_2$): 365
MS (ESI, positive) found: (M+1): 366
MS (ESI, negative) found: (M−1): 364

Example 8

(R)-2-hydroxy-3-(pyridin-3-ylthio)-3,4-dihydro-2H-benzo[e][1,2]oxaborinine-8-carboxylic acid (8)

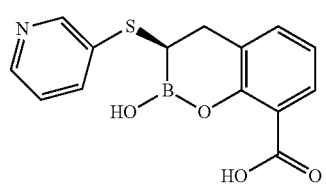

8

¹H NMR (400 MHz, DMSO-d₆) δ 7.80-8.80 (m, 3H), 7.55-7.70 (m, 2H), 7.19-7.32 (m, 1H), 6.74-6.85 (m, 1H), 2.48-3.16 (m, 3H).
MS calcd for ($C_{14}H_{12}BNO_4S$): 301
MS (ESI, positive) found: (M+1): 302
MS (ESI, negative) found: (M+H2O-1): 318

Example 9

(R)-3-(3-amino-3-oxopropylthio)-2-hydroxy-3,4-dihydro-2H-benzo[e][1,2]oxaborinine-8-carboxylic acid (9)

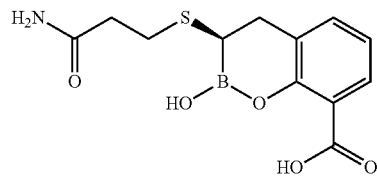

9

¹H NMR (400 MHz, CD₃OD) δ 7.69-7.74 (m, 1H), 7.30-7.35 (m, 1H), 6.77-6.83 (m, 1H), 2.40-3.10 (m, 7H).
MS calcd for ($C_{12}H_{14}BNO_5S$): 295
MS (ESI, positive) found: (M+1): 296
MS (ESI, negative) found: (M−1): 294

Example 10

(R)-2-hydroxy-3-(1-iminoethylthio)-3,4-dihydro-2H-benzo[e][1,2]oxaborinine-8-carboxylic acid (10)

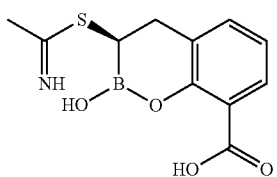

10

¹H NMR (400 MHz, CD₃OD) δ 11.0 (bs, 1H), 7.81 (d, 1H, J=8.0 Hz), 7.31 (d, 1H, J=7.6 Hz), 6.94 (dd, 1H, J=8.0, 8.0 Hz), 3.30 (s, 1H), 2.90-3.12 (m, 2H), 2.30 (s, 3H).
MS calcd for ($C_{11}H_{12}BNO_4S$): 265
MS (ESI, positive) found: (M+1): 266
MS (ESI, negative) found: (M−1): 264

Example 11

(R)-2-hydroxy-3-(thiazol-2-ylthio)-3,4-dihydro-2H-benzo[e][1,2]oxaborinine-8-carboxylic acid (11)

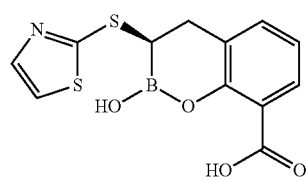

11

¹H NMR (400 MHz, CD₃OD) δ 7.78 (d, 0.5; H, J=4.0 Hz), 7.60-7.65 (m, 1.5H), 4.78-7.50 (m, 1H), 7.23 (d, 1H, J=7.6 Hz), 6.84 (dd, 1H, J=8.0, 16.0 Hz), 3.79-3.90 (m, 1H), 3.15-3.36 (m, 1H), 2.89-2.95 (m, 1H).
MS calcd for ($C_{12}H_{10}BNO_4S_2$): 307
MS (ESI, positive) found: (M+1): 308
MS (ESI, negative) found: (M−H2O-1): 290

Example 12

(R)-3-(1H-1,2,3-triazol-4-ylthio)-2-hydroxy-3,4-dihydro-2H-benzo[e][1,2]oxaborinine-8-carboxylic acid (12)

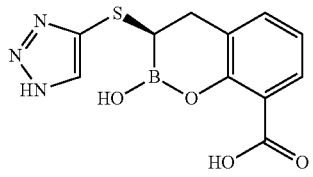

12

¹H NMR (400 MHz, CD₃OD) δ 7.79 (s, 1H), 7.78 (dd, 1H, J=0.8, 8.0 Hz), 7.33 (d, 1H, J=7.6 Hz), 6.92 (dd, 1H, J=8.0, 8.0 Hz), 3.67 (t, 1H, J=4.4 Hz), 3.23 (dd, 1H, J=5.2, 15.2 Hz), 2.95 (dd, 1H, J=3.6, 15.2 Hz).
MS calcd for ($C_{11}H_{10}BN_3O_4S$): 291
MS (ESI, positive) found: (M+1): 292
MS (ESI, negative) found: (M−1): 290

Example 13

(R)-3-(benzyloxy)-2-hydroxy-3,4-dihydro-2H-benzo[e][1,2]oxaborinine-8-carboxylic acid (13)

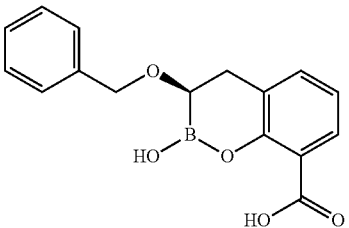

13

(R)-3-(benzyloxy)-2-hydroxy-3,4-dihydro-2H-benzo[e] [1,2]oxaborinine-8-carboxylic acid (13) was prepared following similar procedure described in example 1 (steps 1-5) replacing 2-mercapto-1,3,4-thiadiazole in step 5 with benzyl alcohol to attain benzylated product with a procedure as described in EP1550657.

Final deprotection (step 6) was done by isobutyl boronic acid following general procedure described above.

$^1$H NMR (400 MHz, CD$_3$OD) δ 7.74 (d, 1H, J=8.0 Hz), 7.05-7.37 (m, 6H), 6.84 (dd, 1H, J=4.0, 4.0 Hz), 4.26-4.60 (m, 2H), 3.55 (t, 1H, J=6.4 Hz), 2.94-3.05 (m, 2H).

MS calcd for (C$_{16}$H$_{15}$BO$_5$): 298

MS (ESI, positive) found: (M+1): 299

Example 14

(R)-3-(4-amino-4H-1,2,4-triazol-3-ylthio)-2-hydroxy-3,4-dihydro-2H-benzo[e][1,2]oxaborinine-8-carboxylic acid (14)

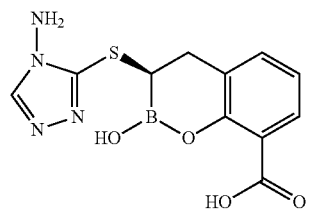

14

$^1$H NMR (400 MHz, CD$_3$OD) δ 8.45 (s, 1H), 7.78 (dd, 1H, J=0.8, 8.0 Hz), 7.33 (d, 1H, J=7.6 Hz), 6.92 (dd, 1H, J=8.0, 8.0 Hz), 3.77 (t, 1H, J=4.4 Hz), 3.23 (dd, 1H, J=5.2, 15.2 Hz).

MS calcd for (C$_{11}$H$_{11}$BN$_4$O$_4$S): 306

MS (ESI, positive) found: (M+1): 307

MS (ESI, negative) found: (M−1): 305

Example 15

Inhibition of Carbapenemase Activity of NDM-1

$K_i$ values of inhibition of NDM-1 were determined spectrophotometrically using three different carbapenems, imipenem, tebipenem and biapenem. NDM-1 preparation was diluted at 1/512, 1/256 and 1/64 ratios (for imipenem, tebipenem and biapenem, respectively) and mixed with various concentrations of beta-lactamase inhibitors (BLIs) in reaction buffer (50 mM sodium phosphate pH7.0, 0.1 mg/ml bovine serum albumin) and incubated for 10 min at 37 C. 100 uM of substrate was added and absorbance profiles were recorded at 294 nm every 1 min for 1 h at 37 C. $K_i$ values were calculated by method of Waley S G (Biochem J. 1982 Sep. 1; 205(3): 631-3). EDTA was used as a positive control. The results of these experiments are presented in Table 1. These experiments demonstrated that several described compounds are potent inhibitors of NDM-1.

TABLE 1

Activity of BLIs ($K_i$, μM) to inhibit cleavage of carbapenems by NDM-1

| Compound | Ki, μM | | |
|---|---|---|---|
| | Imipenem | Tebipenem | Biapenem |
| 1 | Y | Z | Y |
| 2 | X | Y | ND |
| 3 | Z | Z | Z |
| 4 | X | X | X |
| 5 | Y | ND | ND |
| 6 | X | ND | ND |
| 7 | Y | ND | ND |
| 8 | Z | ND | ND |
| 9 | Z | ND | ND |
| 10 | Y | ND | ND |
| 11 | Z | ND | ND |
| 12 | Y | ND | ND |
| 13 | Y | ND | ND |
| 14 | Y | ND | ND |
| EDTA | Y | Y | Y |

X = Less than 0.010 μM
Y = 0.010 μM to 0.1 μM
Z = Greater than 0.1 μM
ND = Not Determined

Example 16

Inhibition of Activity of VIM-1

IC$_{50}$ values of inhibition of VIM-1 were determined spectrophotometrically using nitrocefin (NCF) as reporter substrate. ECM6711 strain carrying pUCP24-VIM-1 plasmid was grown at 37 C to reach OD600=0.6-0.8. Cell suspension was centrifuged for 10 min at 4000 g, supernatant was collected, diluted at 1/64 ratio, mixed with various concentrations of BLIs in reaction buffer and incubated for 10 min at 37 C. 200 uM NCF was added and absorbance profiles were recorded at 490 nm every 30 seconds for 30 min at 37 C. IC$_{50}$ values were calculated as a concentration of BLIs that reduces the rate of NCF degradation by VIM-1 supernatant by 50%. EDTA was used as a positive control. The results of these experiments are presented in Table 2. These experiments demonstrated that several described compounds are potent inhibitors of VIM-1.

TABLE 2

Activity of BLIs (IC50, μM) to inhibit cleavage of Nitrocefin by VIM-1

| Compound | IC$_{50}$, NCF, μM |
|---|---|
| 1 | X |
| 2 | X |
| 3 | Y |
| 4 | X |
| 5 | Y |
| 6 | X |
| 7 | X |
| 8 | X |
| 9 | X |
| 10 | Y |
| 11 | Y |
| 12 | X |
| 13 | X |
| 14 | X |
| EDTA | X |

X = IC$_{50}$ of less than 1.0 μM
Y = IC$_{50}$ of 1.0 μM and above

Example 17

Inhibition of Carbapenemase Activity of Class A, B and D Carbapenemases $K_i$ values of inhibition of purified class A (KPC-2), B (NDM-1) and D (OXA-48) carbapenemases were determined spectrophotometrically using either imipenem (for NDM-1) or biapenem (for KPC-2 and OXA-48) as substrates. Purified enzymes (6 nM and 145 nM for KPC-2 and OXA-48, respectively, 1/512 of NDM-1 enzyme preparation) were mixed with various concentrations of inhibitors in reaction buffer and incubated for 10 min at room temperature. 100 µM of substrate was added and absorbance profiles were recorded at 294 nm every 1 min for 1 hour at 37 C. $K_i$ values were calculated by method of Waley S G (Biochem J. 1982 Sep. 1; 205(3):631-3). The results of these experiments are presented in Table 3. These experiments demonstrated that the described compounds are inhibitors with activity towards carbapenemases from various classes.

TABLE 3

Activity of BLIs (Ki, µM) to inhibit cleavage of carbapenems by purified class A, B and D carbapenemases

| Compound | $K_i$ KPC-2, Biapenem (µM) | $K_i$ OXA-48, Biapenem (µM) | $K_i$ NDM-1, Imipenem (µM) |
|---|---|---|---|
| 1 | Y | Y | Y |
| 2 | Y | Y | X |
| 3 | Y | X | Z |
| 4 | Y | X | X |
| 5 | ND | ND | Y |
| 6 | Y | X | X |
| 7 | ND | X | Y |
| 8 | ND | X | Z |
| 9 | ND | Y | Z |
| 10 | ND | ND | Y |
| 11 | ND | ND | Z |
| 12 | ND | ND | Y |
| 13 | ND | ND | Y |
| 14 | ND | ND | Y |

X = Less than 0.01 µM
Y = 0.01 µM to 0.1 µM
Z = Greater than 0.1 µM
ND = Not Determined

Example 18

Inhibition of Activity of Various Beta-Lactamases

Ki values of inhibition of multiple purified class A, C and D enzymes were determined spectrophotometrically using nitrocefin as reporter substrate. Purified enzymes were mixed with various concentrations of inhibitors in reaction buffer and incubated for 10 min at room temperature. Nitrocefin was added and substrate cleavage profiles were recorded at 490 nm every 10 sec for 10 min. The results of these experiments are presented in Table 4. These experiments confirmed that the described compounds are inhibitors with a broad-spectrum of activity towards various β-lactamases.

TABLE 4

Activity of BLIs (Ki, µM) to inhibit cleavage of nitrocefin by purified class A, C and D enzymes

| Compound | Ki (CTX-M-14, NCF), µM | Ki (SHV-12, NCF), µM | Ki (TEM-10, NCF), µM | Ki (KPC-2, NCF), µM | Ki (P99/AmpC of ECL, NCF), µM | Ki (CMY-2, NCF), µM | Ki (OXA-48, NCF), µM |
|---|---|---|---|---|---|---|---|
| 1 | X | X | X | Y | X | X | X |
| 2 | Y | X | Z | Y | Y | Y | X |
| 3 | X | Y | Z | X | X | X | X |
| 4 | X | X | Y | Y | X | X | X |
| 5 | X | X | X | X | X | X | X |
| 6 | X | X | X | X | X | X | X |
| 7 | X | X | Y | Y | X | X | X |
| 8 | X | X | X | X | X | X | X |
| 9 | X | Y | Z | X | X | X | X |
| 10 | X | X | X | Y | X | X | X |
| 11 | Y | X | Y | Y | X | X | X |
| 12 | X | X | X | Y | X | ND | X |
| 13 | X | X | X | X | X | ND | X |
| 14 | X | X | Y | Y | X | ND | X |
| Tazobactam | X | X | X | Z | Z | Y | Y |
| Clavulanic acid | X | X | X | Z | Z | Z | Z |

X = Less than 0.1 µM
Y = 0.1 µM to 1 µM
Z = Greater than 1 µM
ND = Not Determined

Example 19

Potentiation of Imipenem by Compound 1 Against *E. coli* Strains Expressing Cloned NDM-1 and VIM-1

Carbapenem popentiation activity of Compound 1 was first assessed as its ability to decrease MIC of imipenem of engineered strains of *E. coli* containing plasmids carrying either NDM-1 or VIM-1 genes. Both NDM-1 and VIM-1 expressing strains had increased MIC for imipenem as compared to the strain that contained the vector plasmid alone (Table 5). In the presence of Compound 1 at fixed 4 µg/ml or 8 µg/ml, imipenem MIC of NDM-1 and VIM-1 producing strains was decreased to the level of the strain containing empty vector (Table 5).

TABLE 5

Imipenem Potentiation Activity of Compound 1 against the Strains of *E. coli* Expressing Cloned NDM-1 or VIM-1 Metallo-Beta-lactamases

| | | Imipenem MIC (µg/ml) | | |
|---|---|---|---|---|
| Strain | Plasmid | Alone | w/1 at 4 µg/ml | w/1 at 8 µg/ml |
| ECM6704 | pUCP24 | X | X | X |
| ECM6703 | pUCP24-NDM-1 | Y | X | X |
| ECM6711 | pUCP24-VIM-1 | Y | X | X |

X = MIC of less than 1.0 µg/mL
Y = MIC of 1.0 µg/mL or above

Example 20

Potentiation of Carbapenems by Compound 1 Against Clinical Isolates Strains Expressing Various Class A, B and D Carbapenemases The panel of clinical isolates expressing class A, B and D carbapenemases alone or in combination with other beta-lactamases was used to evaluate carbapenem potentiation activity of Compound 1. MIC for biapenem, doripenem, imipenem and meropenem of these strains was determined either alone or in the presence of Compound 1 at fixed 5 µg/ml in the growth media. The results are present in Table 6. Compound 1 significantly reduced carbapenem MIC of all the strains expressing various carbapenemases.

TABLE 6

Carbapenem Potentiation Activity of Compound 1 against Clinical Isolates Expressing Class A, B and D Carbapenemases

| | | | Biapenem | | Doripenem | | Imipenem | | Meropenem | |
|---|---|---|---|---|---|---|---|---|---|---|
| Strain | Organism | Beta-Lactamases | Alone | w/1 at 5 µg/ml | Alone | w/1 at 5 µg/ml | Alone | w/1 at 5 µg/ml | Alone | w/1 at 5 µg/ml |
| EC1064 | *Escherichia coli* | NDM-1, CMY-6, CTX-M-15 | Z | X | Z | Y | Z | Y | Z | Z |
| KP1081 | *Klebsiella pneumoniae* | NDM-1, TEM-1, SHV-11, CMY-6, CTX-M-15 | Z | X | Z | Y | Z | Y | Z | Y |
| AB1144 | *Acinetobacter baumannii* | NDM-1 | Y | X | Z | Y | Z | Z | Z | Y |
| EA1019 | *Enterobacter aerogenes* | SHV-5, VIM-1 | Z | X | Z | Y | Z | Y | Z | X |
| KP1014 | *Klebsiella pneumoniae* | VIM-1 | Z | Y | Z | Y | Z | Y | Y | X |
| KP1054 | *Klebsiella pneumoniae* | VIM-1, SHV-11 | Z | X | Z | X | Y | Y | Z | X |
| KP1064 | *Klebsiella pneumoniae* | KPC-2, SHV-11, TEM-1 | Z | X | Z | Y | Z | Y | Z | Z |
| KP1074 | *Klebsiella pneumoniae* | KPC-3, SHV-11, TEM | Z | Y | Z | Y | Z | Y | Z | Y |
| KP1084 | *Klebsiella pneumoniae* | KPC-3, SHV-11, TEM-1 | Z | Y | Z | Y | Z | Y | Z | Y |
| KP1004 | *Klebsiella pneumoniae* | KPC-2, TEM-1, SHV-11 | Y | X | Y | X | Z | X | Y | X |
| KP1087 | *Klebsiella pneumoniae* | KPC-2, CTX-M-15, SHV-11, TEM-1 | Z | X | Z | Y | Y | X | Z | Y |

TABLE 6-continued

Carbapenem Potentiation Activity of Compound 1 against Clinical Isolates Expressing Class A, B and D Carbapenemases

| Strain | Organism | Beta-Lactamases | Biapenem | | Doripenem | | Imipenem | | Meropenem | |
|---|---|---|---|---|---|---|---|---|---|---|
| | | | Alone | w/1 at 5 µg/ml | Alone | w/1 at 5 µg/ml | Alone | w/1 at 5 µg/ml | Alone | w/1 at 5 µg/ml |
| KP1086 | Klebsiella pneumoniae | TEM, SHV, CTX-M-15, OXA-48 | Z | X | Z | Y | Z | Y | Z | Y |

X = MIC of less than 1 µg/mL
Y = MIC of 1 µg/mL to 10 µg/mL
Z = MIC of greater than 10 µg/mL Example 21

Potentiation of Biapenem Against Clinical Isolates Strains Expressing Various Class A, B and D Carbapenemases The same panel of clinical strains was used to evaluate biapenem potentiation activity of two other compounds, Compound 3 and Compound 4. The results are present in Table 7. The results indicate that several compounds are capable to potentiate biapenem against clinical strains expressing various carbapenemases.

TABLE 7

Biapenem Potentiation Activity of several BLIs against Clinical Isolates Expressing Class A, B and D Carbapenemases

| Strain | Organism | Beta-Lactamases | Biapenem MIC (µg/ml) | | | |
|---|---|---|---|---|---|---|
| | | | Alone | w/1 at 5 µg/ml | w/4 at 5 µg/ml | w/3 at 5 µg/ml |
| EC1064 | Escherichia coli | NDM-1, CMY-6, CTX-M-15 | Z | X | X | X |
| KP1081 | Klebsiella pneumoniae | NDM-1, TEM-1, SHV-11, CMY-6, CTX-M-15 | Z | X | X | X |
| AB1144 | Acinetobacter baumannii | NDM-1 | Z | X | X | Y |
| EA1019 | Enterobacter aerogenes | SHV-5, VIM-1 | Z | X | X | Y |
| KP1014 | Klebsiella pneumoniae | VIM-1 | Z | Y | Y | Y |
| KP1059 | Klebsiella pneumoniae | VIM-1, SHV-11 | Z | Y | Y | Y |
| KP1054 | Klebsiella pneumoniae | VIM-1, SHV-11 | Z | X | X | X |
| KP1064 | Klebsiella pneumoniae | KPC-2, SHV-11, TEM-1 | Z | X | Y | X |
| KP1074 | Klebsiella pneumoniae | KPC-3, SHV-11, TEM | Z | Y | Y | Y |
| KP1084 | Klebsiella pneumoniae | KPC-3, SHV-11, TEM-1 | Z | Y | Y | Y |
| KP1004 | Klebsiella pneumoniae | KPC-2, TEM-1, SHV-11 | Z | X | X | X |
| KP1087 | Klebsiella pneumoniae | KPC-2, CTX-M-15, SHV-11, TEM-1 | Z | X | Y | X |
| KP1086 | Klebsiella pneumoniae | TEM, SHV, CTX-M-15, OXA-48 | Z | X | Y | X |

X = MIC of less than 1 µg/mL
Y = MIC of 1 µg/mL to 10 µg/mL
Z = MIC of greater than 10 µg/mL Although the invention has been described with reference to embodiments and examples, it should be understood that numerous and various modifications can be made without departing from the spirit of the invention. Accordingly, the invention is limited only by the following claims.

What is claimed is:

1. A compound having the structure of formula I:

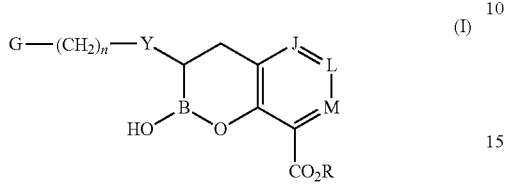

or pharmaceutically acceptable salt thereof, wherein:
Y is selected from the group consisting of —S—, —O—, and —CH$_2$—;
n is 0-3;
G is selected from the group consisting of —C(O)NR$^1$R$^2$; —C(O)NR$^1$OR$^2$; —NR$^1$C(O)R$^2$; —NR$^1$C(O)NR$^2$R$^3$; —NR$^1$C(O)OR$^2$; —NR$^1$S(O)$_2$R$^2$; —NR$^1$S(O)$_2$NR$^2$R$^3$; —C(=NR$^1$)R$^2$; —C(=NR$^1$)NR$^2$R$^3$; —NR$^1$CR$^2$(=NR$^3$); —NR$^1$C(=NR$^2$)NR$^3$R$^4$; aryl optionally substituted with 0-2 substituents selected from the group consisting of C$_{1-4}$ alkyl, —OR$^1$, —NR$^1$R$^2$, halogen, —C(O)NR$^1$R$^2$, and —NR$^1$C(O)R$^2$; heteroaryl optionally substituted with 0-2 substituents selected from the group consisting of C$_{1-4}$ alkyl, —OR$^1$, —NR$^1$R$^2$, halogen, —C(O)NR$^1$R$^2$, and —NR$^1$C(O)R$^2$; and heterocyclyl optionally substituted with 0-2 substituents selected from the group consisting of C$_{1-4}$ alkyl, —OR$^1$, —NR$^1$R$^2$, halogen, —C(O)NR$^1$R$^2$, and —NR$^1$C(O)R$^2$;
J, L, and M are each independently selected from the group consisting of CR$^7$ and N;
R is selected from a group consisting of —H, —C$_{1-9}$alkyl, —CR$^5$R$^6$OC(O)C$_{1-9}$alkyl, —CR$^5$R$^6$OC(O)OC$_{1-9}$alkyl, and

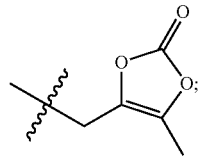 [SMILES: *Cc1oc(=O)oc1C]

R$^1$, R$^2$, R$^3$, R$^4$, R$^5$ and R$^6$ are each independently selected from —H and —C$_{1-4}$alkyl; and
R$^7$ is selected from the group consisting of —H, —C$_{1-4}$alkyl, —OH, —OC$_{1-4}$alkyl, and halogen.

2. The compound of claim 1, having the structure of (Ia):

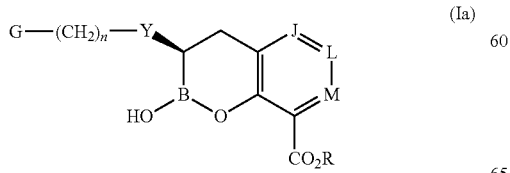

or pharmaceutically acceptable salt thereof.

3. The compound of claim 1, having the structure of (Ib):

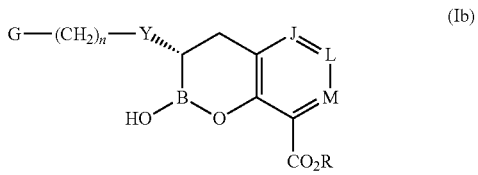

or pharmaceutically acceptable salt thereof.

4. The compound of claim 1, wherein n is 0 or 1.

5. The compound of claim 1, wherein:
Y is O or S;
G is selected from the group consisting of phenyl, imidazole, pyrazole, triazole, tetrazole, thiazole, thiadiazole, oxazole, oxadiazole, isoxazole, isothiazole, pyridine, pyrazine, pyrimidine, pyridazine, and pyrazine, each optionally substituted by 0-2 substituents selected from the group consisting of —OR$^1$, —NR$^1$R$^2$, halogen, —C(O)NR$^1$R$^2$, and —NR$^1$C(O)R$^2$; and
J, L and M are CR$^7$.

6. The compound of claim 5, wherein n is 0.

7. The compound of claim 5, wherein G is thiadiazole.

8. The compound of claim 5, wherein G is thiadiazole optionally substituted with NR$^1$R$^2$ or —NR$^1$C(O)R$^2$, wherein R$^1$ and R$^2$ are independently H or —C$_{1-4}$alkyl.

9. The compound of claim 5, wherein G is triazole optionally substituted with NR$^1$R$^2$, wherein R$^1$ and R$^2$ are independently H or —C$_{1-4}$alkyl.

10. The compound of claim 5, wherein G is tetrazole optionally substituted with methyl.

11. The compound of claim 5, wherein G is pyridine.

12. The compound of claim 5, wherein G is thiazole.

13. The compound of claim 5, wherein G is phenyl.

14. The compound of claim 1, wherein:
Y is S;
n is 1 or 2;
G is —C(O)NR$^1$R$^2$ or —C(=NR$^1$)R$^2$; and
J, L and M are CR$^7$.

15. The compound of claim 14, wherein R$^7$ is H.

16. The compound of claim 14, wherein R' is H and R$^2$ is H.

17. The compound of claim 1, wherein G is selected from the group consisting of —C(O)NR$^1$R$^2$; —C(O)NR$^1$OR$^2$; —NR$^1$C(O)R$^2$; —NR$^1$C(O)NR$^2$R$^3$; —NR$^1$C(O)OR$^2$; —NR$^1$S(O)$_2$R$^2$; —NR S(O)$_2$NR$^2$R$^3$; —C(=NR$^1$)NR$^2$R$^3$; —NR$^1$CR$^2$(=NR$^3$); C(=NR$^2$)NR$^3$R$^4$; aryl optionally substituted with 0-2 substituents selected from the group consisting of —OR$^1$, —NR$^1$R$^2$, halogen, —C(O)NR$^1$R$^2$, and —NR$^1$C(O)R$^2$; heteroaryl optionally substituted with 0-2 substituents selected from the group consisting of —OR$^1$, —NR$^1$R$^2$, halogen, —C(O)NR$^1$R$^2$, and —NR$^1$C(O)R$^2$; and heterocyclyl optionally substituted with 0-2 substituents selected from the group consisting of —OR$^1$, —NR$^1$R$^2$, halogen, —C(O)NR$^1$R$^2$, and —NR$^1$C(O)R$^2$.

18. The compound of claim 1, having the structure selected from the group consisting of:

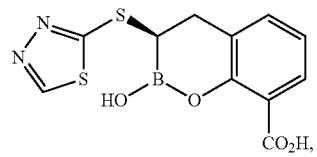

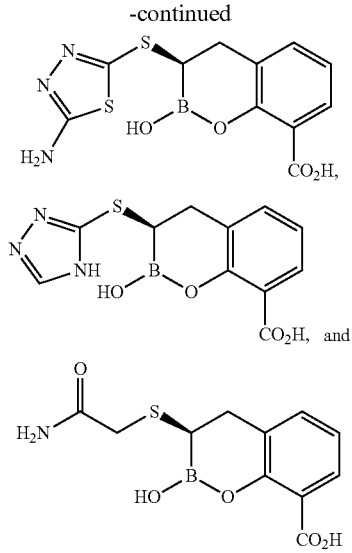

or pharmaceutically acceptable salts thereof.

19. The compound of claim 1, having the structure selected from the group consisting of:

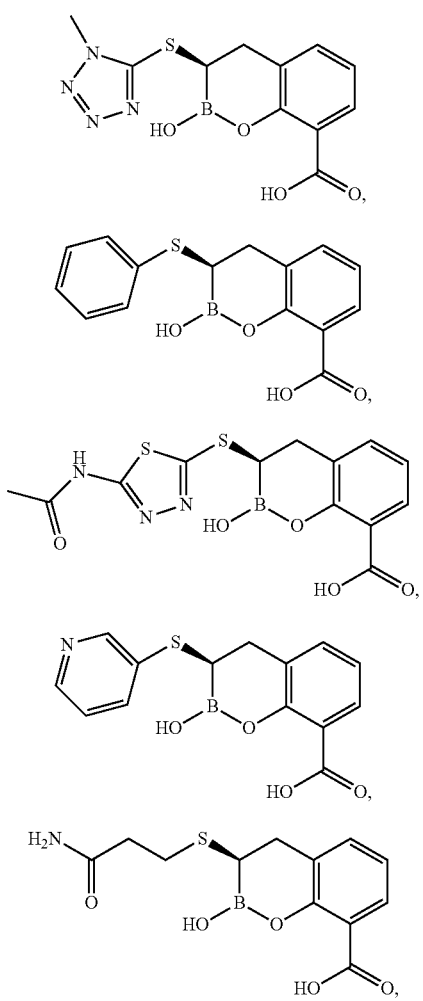

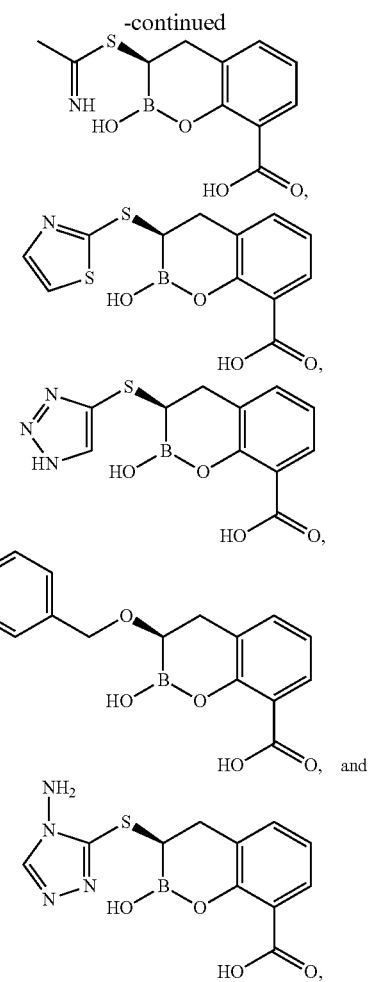

or pharmaceutically acceptable salts thereof.

20. A pharmaceutical composition comprising a therapeutically effective amount of a compound of claim 1 and a pharmaceutically acceptable excipient.

21. The pharmaceutical composition of claim 20, further comprising an additional medicament.

22. The composition of claim 21, wherein the additional medicament is selected from an antibacterial agent, antifungal agent, an antiviral agent, an anti-inflammatory agent, or an anti-allergic agent.

23. The composition of claim 22, wherein the additional medicament is a β-lactam antibacterial agent.

24. The composition of claim 23, wherein the β-lactam is selected from Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid,Ceforanide, Cefotiam, Cefprozil, Cefbuperazone, Cefuroxime, Cefuzonam, Cefoxitin, Cefotetan, Cefmetazole, Loracarbef, Cefixime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04,546, ME1036, Ceftiofur, Cefquinome, Cefovecin, RWJ-442831, RWJ-333441, or RWJ-333442.

25. The composition of claim 23, wherein the β-lactam is selected from Ceftazidime, Biapenem, Doripenem, Ertapenem, Imipenem, Meropenem, or Panipenem.

26. The composition of claim 23, wherein the β-lactam is selected from Aztreonam, Tigemonam, BAL30072, SYN 2416, or Carumonam.

27. A method of treating or preventing a bacterial infection, comprising administering to a subject in need thereof, a compound according to claim 1, wherein the bacterial infection comprises a bacteria that produces a carbapenemase.

28. The method of claim 27, further comprising administering to the subject an additional medicament.

29. The method of claim 28, wherein the additional medicament is selected from an antibacterial agent, antifungal agent, an antiviral agent, an anti-inflammatory agent, or an anti-allergic agent.

30. The method of claim 29, wherein the additional medicament is a β-lactam antibacterial agent.

31. The method of claim 30, wherein the β-lactam is selected from Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04,546, ME1036, Ceftiofur, Cefquinome, Cefovecin, RWJ-442831, RWJ-333441, or RWJ-333442.

32. The method of claim 30, wherein the β-lactam is selected from Ceftazidime, Biapenem, Doripenem, Ertapenem, Imipenem, Meropenem, or Panipenem.

33. The method of claim 30, wherein the β-lactam is selected from Aztreonam, Tigemonam, BAL30072, SYN 2416, or Carumonam.

34. The method of claim 27, wherein the subject is a mammal.

35. The method of claim 34, wherein the mammal is a human.

36. The method of claim 27, wherein the bacteria is selected from *Pseudomonas acidovorans, Pseudomonas alcaligenes, Pseudomonas putida, Burkholderia cepacia, Aeromonas hydrophilia, Francisella tularensis, Morganella morganii, Proteus mirabilis, Proteus vulgaris, Providencia alcalifaciens, Providencia rettgeri, Providencia stuartii, Acinetobacter baumannii, Bordetella pertussis, Bordetella parapertussis, Bordetella bronchiseptica, Haemophilus ducreyi, Pasteurella multocida, Pasteurella haemolytica, Branhamella catarrhalis, Borrelia burgdorferi, Kingella, Gardnerella vaginalis, Bacteroides distasonis, Bacteroides 3452A homology group, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus*.

37. The method of claim 27, wherein the bacteria is selected from *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii,* or *Bacteroides splanchnicus*.

* * * * *